United States Patent
DeJovin et al.

(10) Patent No.: US 7,439,241 B2
(45) Date of Patent: *Oct. 21, 2008

(54) COMPOUNDS, FORMULATIONS, AND METHODS FOR TREATING OR PREVENTING ROSACEA

(75) Inventors: Jack A. DeJovin, New Brunswick, NJ (US); Isabelle Jean DeJovin, New Brunswick, NJ (US)

(73) Assignee: Galderma Laboratories, Inc., Fort Worth, TX (US)

( * ) Notice: Subject to any disclaimer, the term of this patent is extended or adjusted under 35 U.S.C. 154(b) by 457 days.

This patent is subject to a terminal disclaimer.

(21) Appl. No.: 10/853,585

(22) Filed: May 25, 2004

(65) Prior Publication Data
US 2004/0242588 A1 Dec. 2, 2004

Related U.S. Application Data

(60) Provisional application No. 60/473,611, filed on May 27, 2003.

(51) Int. Cl.
*A61K 31/50* (2006.01)
*A61K 31/415* (2006.01)
*A01N 43/60* (2006.01)
*A01N 43/50* (2006.01)

(52) U.S. Cl. .................. 514/249; 514/401; 514/649; 514/651

(58) Field of Classification Search .................. 514/249, 514/230.5
See application file for complete search history.

(56) References Cited

U.S. PATENT DOCUMENTS

| | | | |
|---|---|---|---|
| 3,560,501 A | 2/1971 | Walker |
| 3,594,380 A | 7/1971 | Sulkowski |
| 3,723,432 A | 3/1973 | Ott |
| 3,736,297 A | 5/1973 | Bracke |
| 3,740,442 A | 6/1973 | Ott |
| 3,890,319 A | 6/1975 | Danielewicz et al. |
| 4,029,792 A | 6/1977 | Danielewicz et al. |
| 4,164,570 A | 8/1979 | Clough et al. |
| 4,201,211 A | 5/1980 | Chandrasekaran et al. |
| 4,285,967 A | 8/1981 | Gubernick et al. |
| 5,021,416 A | 6/1991 | Gluchowski |
| 5,077,292 A | 12/1991 | Gluchowski |
| 5,112,822 A | 5/1992 | Gluchowski |
| 5,130,441 A | 7/1992 | Gluchowski |
| 5,198,442 A | 3/1993 | Gluchowski |
| 5,204,347 A | 4/1993 | Gluchowski |
| 5,237,072 A | 8/1993 | Gluchowski |

(Continued)

FOREIGN PATENT DOCUMENTS

GB  1381979  1/1975

(Continued)

OTHER PUBLICATIONS

Wymenga, A.N. et al., Management of Hot Flushes in Breast Cancer Patients, Acta Ocologica, 2002, vol. 41, No. 3, pp. 269-275.

(Continued)

*Primary Examiner*—Michael G. Hartley
*Assistant Examiner*—Blessing Fubara
(74) *Attorney, Agent, or Firm*—Hoffmann & Baron, LLP

(57) ABSTRACT

In methods, compounds, and topical formulations for treatment of rosacea incorporating compounds represented by the formulas below:

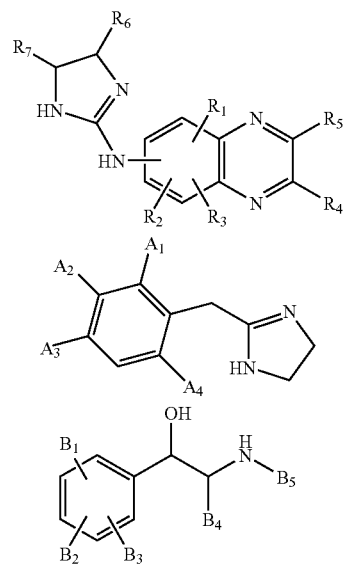

wherein each of $R_1$, $R_2$, and $R_3$ is independently hydrogen, hologen, alkyl, or alkoxy;
each of $R_4$ and $R_5$ is independently hydrogen, alkyl, or alkoxy; and each of $R_6$ and $R_7$ is independently hydrogen, nitro, alkyl, or alkoxy;
wherein each of $A_1$, $A_3$, and $A_4$ is independently hydrogen or alkyl; and $A_2$ is independently hydrogen or hydroxy; and
wherein each of $B_1$, $B_2$, and $B_3$ is independently hydrogen, hydroxy, or alkoxy; and each of $B_4$ and $B_5$ is independently hydrogen or alkyl, applying such compounds topically as sprays, mists, aerosols, solutions, lotions, gels, creams, ointments, pastes, unguents, emulsions, and suspensions to treat rosacea and its symptoms.

1 Claim, No Drawings

U.S. PATENT DOCUMENTS

| | | | |
|---|---|---|---|
| 5,300,504 | A | 4/1994 | Gluchowski |
| 5,326,763 | A | 7/1994 | Gluchowski et al. |
| 5,373,010 | A | 12/1994 | Gluchowski et al. |
| 5,418,234 | A | 5/1995 | Gluchowski et al. |
| 5,424,078 | A | 6/1995 | Dziabo et al. |
| 5,442,053 | A | 8/1995 | Della Valle et al. |
| 5,552,403 | A | 9/1996 | Burke et al. |
| 5,561,132 | A | 10/1996 | Burke et al. |
| 5,587,376 | A | 12/1996 | Burke et al. |
| 5,693,646 | A | 12/1997 | Jones et al. |
| 5,696,127 | A | 12/1997 | Jones et al. |
| 5,703,077 | A | 12/1997 | Burke et al. |
| 5,714,486 | A | 2/1998 | Burke et al. |
| 5,720,962 | A | 2/1998 | Ivy et al. |
| 5,721,237 | A | 2/1998 | Myers et al. |
| 5,736,165 | A | 4/1998 | Ripley et al. |
| 5,753,637 | A | 5/1998 | Fried |
| 5,756,503 | A | 5/1998 | Burke et al. |
| 5,773,440 | A | 6/1998 | Burke et al. |
| 6,117,871 | A | 9/2000 | Maurer et al. |
| 6,117,877 | A | 9/2000 | Fogel |
| 6,194,415 | B1 | 2/2001 | Wheeler et al. |
| 6,248,741 | B1 | 6/2001 | Wheeler et al. |
| 6,284,765 | B1 | 9/2001 | Caffrey |
| 6,294,553 | B1 * | 9/2001 | Gil et al. ............ 514/314 |
| 6,323,204 | B1 | 11/2001 | Burke et al. |
| 6,432,934 | B1 * | 8/2002 | Gilbard ............ 514/152 |
| 6,441,047 | B2 | 8/2002 | Desantis, Jr. |
| 6,444,681 | B1 | 9/2002 | Flavahan et al. |
| 6,465,464 | B2 | 10/2002 | Wheeler et al. |
| 6,534,048 | B1 | 3/2003 | Borgman |
| 2002/0197300 | A1 | 12/2002 | Schultz et al. |
| 2003/0068343 | A1 | 4/2003 | Muizzuddin et al. |
| 2003/0077301 | A1 | 4/2003 | Maibach et al. |
| 2003/0087962 | A1 | 5/2003 | Demopulos et al. |
| 2003/0229088 | A1 * | 12/2003 | Gil et al. ............ 514/230.5 |
| 2004/0092482 | A1 | 5/2004 | Gupta |
| 2004/0156873 | A1 | 8/2004 | Gupta |
| 2004/0220259 | A1 | 11/2004 | Yu et al. |
| 2004/0242588 | A1 | 12/2004 | Dejovin et al. |
| 2004/0254252 | A1 | 12/2004 | Engles et al. |
| 2004/0266776 | A1 | 12/2004 | Gil et al. |
| 2005/0020600 | A1 | 1/2005 | Scherer |
| 2005/0165079 | A1 | 7/2005 | Shanler et al. |

FOREIGN PATENT DOCUMENTS

| | | |
|---|---|---|
| WO | WO 96/25163 A1 | 8/1996 |
| WO | WO 98/36730 A3 | 8/1998 |
| WO | WO 00/76502 A1 | 12/2000 |

OTHER PUBLICATIONS

Scruggs, Jennifer T., et al., The Teardrop Sign: a Rare Dermatological Reaction to Brimonidine, *Br J Ophthalmol*, Jun. 2000, V. 84, pp. 671-672.

Sakakibara, R. et al., Treatment of Primary Erythromelalgia with Cyproheptadine, *Journal of the Autonomic Nervous System*, V. 58, Nos. 1+2, Apr. 20, 1996, pp. 121-122.

Jeyara, J., Selvi C., et al., Cooling Evokes Redistribution of $\alpha_{2c}$-Adrenoceptors from Golgi to Plasma Membrane in Transfected Human Embryonic Kidney 293 Cells, *Molecular Pharmacology*, V. 60, No. 6, Dec. 2001, pp. 1195-1200.

Fuchs, Perry N., et al., Heat, but not Mechanical Hyperalgesia, following Adrenergic Injections in Normal Human Skin, *Pain*, V. 90, Nos. 1-2, Feb. 1, 2001, pp. 15-23.

Morrison, Shaun F., et al., Adrenergic Modulation of a Spinal Sympathetic Reflex in the Rat, *J. Pharmacol. Experim. Therap.*, V. 273, No. 1, 1995, pp. 380-385.

Yaksh, Tony Y., et al., Reversal of Nerve Ligation-Induced Allodynia by Spinal *Alpha*-2 Adrenoceptor Agonists, *J. Pharmacol. Experim. Therap.*, V. 272, No. 1, 1995, pp. 207-214.

Waldron, C.J., et al., Relative Contribution of Different Vascular Beds to the Pressor Effects of $\alpha$-Adrenoceptor Agonists and Vasopressin in Pithed Rats: Radioactive Microsphere Determination, *J. Auton. Pharmac.*, 1985, V. 5, pp. 333-338.

Bockman et al. "Binding and Functional Characterization of Alpha-2-Adrenergic Receptor Subtypes on Pig Vascular Endothelium," J. Pharmacol. Exp. Therapeutics, 1993, vol. 267, pp. 1126-1133.

Burke and Schwartz, "Preclinical Evaluation of Brimonidine," Survey of Ophthalmology, 1996, vol. 41, pp. S9-S18.

Chein et al., "Corneal and conjuctival/scleral penetration of p-aminoclonidine, AGN 190342, and clonidine in rabbit eyes," Current Eye Research, 1990, vol. 9, No. 11, pp. 1051-1059.

Chotani et al. "Silent $\alpha_{sc}$-adrenergic receptors enable cold-induced vasoconstriction in cutaneous arteries," Am. J. Physiol. Heart Circ. Physiol., 2000, vol. 278, pp. H1075-H1083.

Freedman and Blacker, "Estrogen raises the sweating threshold in postmenopausal women with hot flashes," Fertility and Sterility, 2002, vol. 77, No. 3, pp. 487-490.

Guarrera et al., "Flushing in Rosacea: A Possible Mechanism," Arch. Dermatol. Res. 1982, vol. 272, pp. 311-316.

Nakamura and Ferreira, "Peripheral analgesic action of clonidine: mediation by release of endogenous enkephlin-like substances," European Journal of Pharmacology, 1988, vol. 146, pp. 223-228.

Nielsen et al., "Postjunctional $\alpha_2$-adrenoceptors mediate vasoconstriction in human subcutaneous resistance vessels," Br. J. Pharmacol., 1989, vol. 97, pp. 829-834.

Walters, "Development and Use of Brimonidine in Treating Acute and Chronic Elevations of Intraocular Pressure: A Review of Safety, Efficacy, Dose Response, and Dosing Studies," Survey of Ophthalmology, 1996, vol. 41, pp. S19-S26.

Wilkin, "Effect of Subdepressor Clonidine on Flushing Reactions in Rosacea," Arch. Dermatol., 1983, vol. 119, pp. 211-214.

Wilkin, "Why is flushing limited to a mostly facial cutaneous distribution?" J. Am. Acad. Dermatol., 1988, vol. 19, pp. 309-313.

Arndt et al., Manual of Dermatologic Therapeutics 7th ed., 176-177, (2007).

Cunliffe et al., Br. Med. J. 105 (Jan. 8, 1977).

Shanler et al., Arch Dermatol, 143(11):1369-1371(Nov. 2007).

Wilkin et al., J. Am. Acad. Dermatol. 46:584-587 (2002).

Webster, Guy F., "Rosacea and related disorders" Dermatology, J. Bolognia, J. Jorizzo, R. Rapini eds, vol. 1, Chpt. 39, pp. 545-552 (2003).

* cited by examiner

COMPOUNDS, FORMULATIONS, AND METHODS FOR TREATING OR PREVENTING ROSACEA

CROSS REFERENCE TO RELATED APPLICATION

This application claims priority from U.S. patent application Ser. No. 60/473,611, filed on May 27, 2003.

FIELD OF THE INVENTION

The present invention is directed to compounds and methods for treatment or prevention of rosacea. The compounds and methods taught by the present invention are particularly useful for treating or preventing rosacea and the symptoms of rosacea.

BACKGROUND OF THE INVENTION

Many people are affected by inflammatory skin disorders that result in unsightly and painful rashes, acne, persistent red veins, and acne-like skin eruptions, such as macules, nodules, and pustules that may ooze or crust. Inflammatory skin disorders often result in intense psychosocial distress. Rosacea is a common inflammatory skin disorder affecting over 10 million people in the United States. Rosacea generally involves the cheeks, nose, chin, and forehead and the typical age of onset is 30 to 60 years. See e.g., Zuber T. J., *Rosacea: Beyond First Blush* 32 HOSP. PRACT. 188-189 (1997); THE MERCK MANUAL 813-814 (Keryn A. G. Lane et al. eds. $17^{th}$ ed. 2001). Many people with early-stage rosacea incorrectly assume that they suffer from adult acne, sun or windburn, or the normal effects of aging.

Rosacea develops gradually starting as frequent blushing and frequent irritation of the facial skin. More advanced rosacea is characterized by a vascular stage where patients display increasingly severe erythema (abnormal redness of the skin) and telangiectasia (visible red lines due to abnormal dilatation of capillary vessels and arterioles). Pimple-like eruptions, which may be solid (called papules or nodules) or puss filled (known as pustules) may develop. Such eruptions often look like acne, but whiteheads or blackheads (common symptoms of acne) are not normally present. Later-stage rosacea is characterized by rhinophyma (enlargement of the nose). If left untreated, rosacea can progress to irreversible disfigurement. Rosacea symptoms are often aggravated by sun exposure, changes or extremes in temperature, wind, and consumption of certain foods, such as spicy foods, caffeine, and alcohol.

The exact pathogenesis of rosacea is unknown, but the pathologic process is well described. For example, erythema associated with rosacea is caused by dilation of the superficial vasculature of the face. Zuber T. J., *Rosacea: Beyond First Blush* 32 HOSP. PRACT. 188-189 (1997).

There is no known cure for rosacea. Current treatments, which are directed to control of redness, inflammation, and skin eruptions, are of limited effectiveness in many patients and, generally, can be used only for a limited duration. Standard treatments include avoidance of triggers such as sun exposure, wind exposure, alcohol consumption, spicy foods, and irritating facial cleansers, lotions, and cosmetics. Antibiotics are the traditional first line of therapy. Long-term treatment (5 to 8 weeks or more) with oral antibiotics such as tetracycline, minocycline, doxycycline or clarithromycin may control skin eruptions. Alternative oral treatments include vitamin A medications, such as isoretinoin and antifungal medications. Unfortunately, such oral medications often cause side effects and many people have limited tolerance. Topical treatments, such at topically applied antibiotics and antifungals (such as metronidazole) or steroids, are available but also have limited effectiveness and cannot treat all symptoms. For example, isoretinoin has serious teratogenic side-effects and female patients of child bearing age must use effective birth control or avoid the therapy. Topical treatments include topically applied metronidazole, topically applied steroids, topically applied azelaic acid, topically applied rentinoic acid or retinaldehyde, and topical vitamin C preparations are available but have limited effectiveness and cannot treat all symptoms. Surgery, such as the laser elimination of blood vessels, is typically a last resort, but may be prescribed if other treatments are ineffective. In patients with nose hyperplasia, surgical reduction may improve the patient's cosmetic appearance, but does not treat the disease itself. Mixed light pulse (photoderm) therapy has proved somewhat effective for certain rosacea symptoms in some patients. Thus, there remains a need for topical formulations for treatment of rosacea and its symptoms.

Agonists of the $\alpha_2$ adrenoceptors have been used therapeutically for a number of conditions including hypertension, congestive heart failure, angina pectoris, spasticity, glaucoma, diarrhea, and for the suppression of opiate withdrawal symptoms (J. P. Heible and R. R. Ruffolo Therapeutic Applications of Agents Interacting with $\alpha$-Adrenoceptors, p. 180-206 in Progress in Basic and Clinical Pharmacology Vol. 8, P. Lomax and E. S. Vesell Ed., Karger, 1991).

Adrenoceptor agonists such as clonidine have been primarily used orally, though a patch formulation is known. The goal of existing formulations is to deliver a systemic internal dose of the compound to the patient. The $\alpha_2$ agonists are known to mediate vasoconstriction both in the core and periphery of a patient. In particular $\alpha_2$ adrenoceptor agonists are known to cause vasoconstriction of peripheral arterioles, in response to stimulation due to cold or stress.

A number of patents describe the use of brimonidine for treating ophthalmic conditions and eye diseases. In Canadian patent No. CA2326690, there is described the use of topical ophthalmic preparations for use only in the eyes, to treat eye diseases. The Canadian patent discusses the problems with ophthalmic preparations taken topically (in the eye), orally or parenterally, and their systemic effects, including some serious, that limit their use. These systemic effects include, cardiopulmonary effects of β-blockers like timolol; dryness of mouth, flush, fever, tachy cardia, urinary retention, convulsion and irritability with atropine; hypertension with phenylephine; increased salivation, nausea, vomiting, diarrhea, stomach cramps, bronchial secretions, brionchial constriction, asthma, bradycardia, paresthesia with miotics; hypotension with clonidine; and dry mouth, fatigue and drowsiness with apraclonidine and brimonidine.

There has been no composition containing $\alpha_2$ adrenoceptor agonists that can deliver a dose of the agonist to the patient, ameliorating the symptoms of rosacea, without causing systemic side effects. There has also been no topical skin composition containing $\alpha_2$ adrenoceptor agonists that can deliver a dose of the agonist to the skin of the patient, ameliorating the symptoms of rosacea, without causing systemic side effects.

SUMMARY OF THE INVENTION

The present invention provides methods, compounds, and topical skin formulations for treatment of rosacea and its symptoms. Compounds of the invention are $\alpha_2$ adrenoceptor agonists that act on the peripheral vasculature to cause vasoconstriction and thereby ameliorate the symptoms of rosacea. The compounds are delivered in a topical skin composition that insures that the compounds are effective in the skin of a patient but do not penetrate the skin in sufficient amounts to induce serious systemic side effects.

Compounds of one embodiment of the invention are represented by Formula I below:

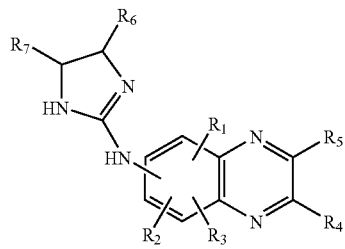

I wherein each of $R_1$, $R_2$, and $R_3$ is independently hydrogen, halogen, alkyl, preferably, unsubstituted alkyl, or alkoxy, preferably, unsubstituted alkoxy; each of $R_4$ and $R_5$ is independently hydrogen, alkyl, preferably, unsubstituted alkyl, or alkoxy, preferably, unsubstituted alkoxy; and each of $R_6$ and $R_7$ is independently hydrogen, nitro, alkyl, preferably, unsubstituted alkyl, or alkoxy, preferably, unsubstituted alkoxy. In a preferred embodiment of the compounds of Formula I, $R_6$ and $R_7$ are both hydrogen. In another preferred embodiment, $R_4$ and $R_5$ are both hydrogen.

To treat or prevent rosacea, according to the methods of the invention, the compounds of this embodiment of the invention are topically applied. Preferably the compounds of the invention are delivered in a topical formulation. Formulations for topical delivery of compounds of the invention are well-known in the art, such as aqueous or non-aqueous solutions or suspensions, creams, lotions, gels, or ointments.

Compounds of another embodiment of the invention are represented by Formula II below:

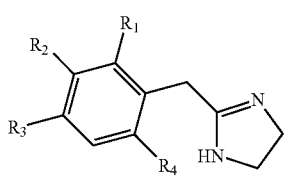

II

Compounds of another embodiment of the invention are represented by Formula III below:

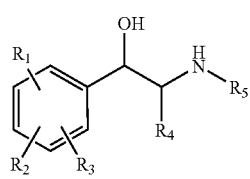

III

Compounds of other embodiments of the invention are shown below:

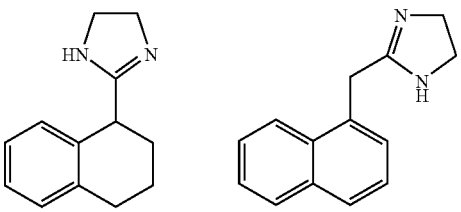

These and other features, aspects, and advantages of the present invention will become better understood with reference to the following detailed description, examples, and claims.

These and other features, aspects, and advantages of the invention will become better understood with reference to the following detailed description, examples, and appended claims.

DETAILED DESCRIPTION 1.1 Compounds of the Invention

In one embodiment, the invention is directed to compounds of the Formula I:

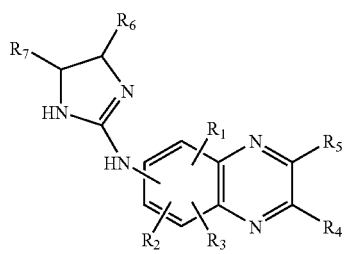

I wherein each of $R_1$, $R_2$, and $R_3$ is independently hydrogen, halogen, alkyl, preferably, unsubstituted alkyl, or alkoxy, preferably, unsubstituted alkoxy; each of $R_4$ and $R_5$ is independently hydrogen, alkyl, preferably, unsubstituted alkyl, or alkoxy, preferably, unsubstituted alkoxy; and each of $R_6$ and $R_7$ is independently hydrogen, nitro, alkyl, preferably, unsubstituted alkyl, or alkoxy, preferably, unsubstituted alkoxy. In a preferred embodiment of the compounds of Formula I, $R_6$ and $R_7$ are both hydrogen. In another preferred embodiment, $R_4$ and $R_5$ are both hydrogen.

In another embodiment, the invention is directed to compounds of the Formula Ia;

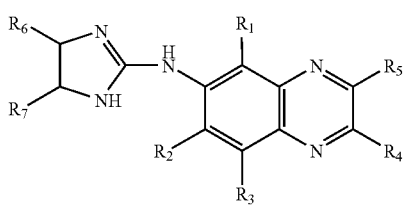

Ia wherein each of $R_1$, $R_2$, and $R_3$ is independently hydrogen, halogen, alkyl, preferably, unsubstituted alkyl, or alkoxy, preferably, unsubstituted alkoxy; each of $R_4$ and $R_5$ is independently hydrogen, alkyl, preferably, unsubstituted alkyl, or alkoxy, preferably, unsubstituted alkoxy; and each of $R_6$ and $R_7$ is independently hydrogen, nitro, alkyl, preferably, unsubstituted alkyl, or alkoxy, preferably, unsubstituted alkoxy. In a preferred embodiment of the compounds of Formula Ia, $R_6$ and $R_7$ are both hydrogen. In another preferred embodiment, $R_4$ and $R_5$ are both hydrogen. In still another preferred embodiment of the compounds of Formula Ia, $R_2$ and $R_3$ are both hydrogen and $R_1$ is halo, preferably, bromo.

In another embodiment, the invention relates to compounds of the Formula Ib:

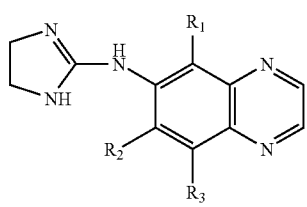

Ib wherein each of $R_1$, $R_2$, and $R_3$ is independently hydrogen, halogen, alkyl, preferably, unsubstituted alkyl, or alkoxy, preferably, unsubstituted alkoxy. In a preferred embodiment of the compounds of Formula Ib, $R_2$ and $R_3$ are both hydrogen and $R_1$ is halo, preferably, bromo.

In another embodiment, the invention relates to compounds of the Formula Ic:

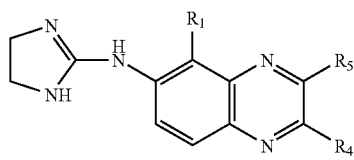

Ic wherein $R_1$ is hydrogen, halogen, alkyl, preferably, unsubstituted alkyl, or alkoxy, preferably unsubstituted alkoxy. In a preferred embodiment $R_1$ is halo, more preferably, bromo; and each of $R_4$ and $R_5$ is independently hydrogen, alkyl, preferably, unsubstituted alkyl, or alkoxy, preferably, unsubstituted alkoxy. In a preferred embodiment of the compounds of Formula Ic, at least one of $R_4$ and $R_5$ is hydrogen.

In another embodiment, the invention relates to compounds of the Formula Id:

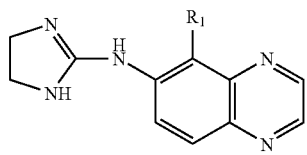

Id wherein $R_1$ is hydrogen, halogen, alkyl, preferably, unsubstituted alkyl, or alkoxy, preferably, unsubstituted alkoxy. In a preferred embodiment, $R_1$ is halo, more preferably, bromo.

In another embodiment, the invention relates to compounds of the Formula II:

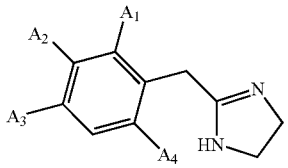

II wherein each of $A_1$, $A_3$, and $A_4$ is independently hydrogen or alkyl, and $A_2$ is hydrogen or hydroxyl.

In another embodiment, the invention relates to compounds of the Formula III:

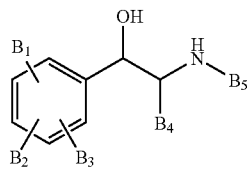

III wherein each of $B_1$, $B_2$, and $B_3$ is independently hydrogen, hydroxy, or methoxy; each of $B_4$ and $B_5$ is independently hydrogen or alkyl.

Preferred compounds of the invention are listed in Table 1 below.

TABLE 1

Compounds Of The Invention

| Compound of the Invention | Name |
|---|---|
| 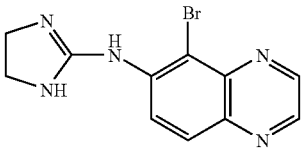 | (5-Bromo-quinoxalin-6-yl)-(4,5-dihydro-1H-imidazol-2-yl)-amine (Brimonidine) |
| 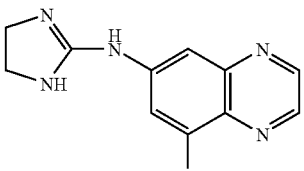 | (8-Bromo-quinoxalin-6-yl)-(4,5-dihydro-1H-imidazol-2-yl)-amine |
| 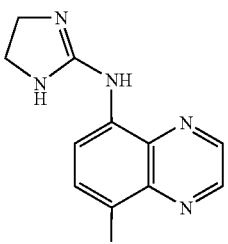 | (8-Bromo-quinoxalin-5-yl)-(4,5-dihydro-1H-imidazol-2-yl)-amine |

TABLE 1-continued

Compounds Of The Invention

| Compound of the Invention | Name |
|---|---|
| | (5-Bromo-3-methyl-quinoxalin-6-yl)-(4,5-dihydro-1H-imidazol-2-yl)-amine |
| | (5-Bromo-2-methoxy-quinoxalin-6-yl)-(4,5-dihydro-1H-imidazol-2-yl)-amine |
| | (4,5-dihydro-1H-imidazol-2-yl)-(8-methyl-quinoxalin-6-yl)-amine |
| | (4,5-dihydro-1H-imidazol-2-yl)-quinoxalin-5-yl-amine |
| | Tetrahydrozaline |
| | Naphazoline |
| | Oxymetazoline |
| | Xylometazoline |
| | Epinephrine |
| | Norepinephrine |
| | Phenylephrine |
| | Methoxyamine |

The most preferred compound is (5-Bromo-quinoxalin-6-yl)-(4,5-dihydro-1H-imidazol-2-yl)-amine (commonly referred to as brimonidine) and pharmaceutically acceptable salts thereof, particularly the tartrate salt. Other compounds of the invention include naphazoline, tetra-hydrozaline, oxymetazoline, xylometazoline, epinephrine, norepinephrine, phenylephrine and methoxamine and their pharmaceutically acceptable salts.

The compounds of the invention are well known in the art to be $\alpha_2$ adrenergic receptor agonists. As such the compounds have powerful vasoconstricting effects when introduced into the body of mammals, particularly humans.

1.2 Synthesis of Compounds of the Invention

The compounds of the invention can be prepared in accordance with well-known synthetic procedures, for example, using the general synthetic procedures outlined in U.S. Pat. Nos. 3,890,319 (issued Jun. 17, 1975) and U.S. Pat. No. 4,029,792 (issued Jun. 14, 1977) both of which patents are hereby incorporated herein by reference. Scheme 1 below illustrates one method to synthesize compounds of Formula I.

Scheme 1

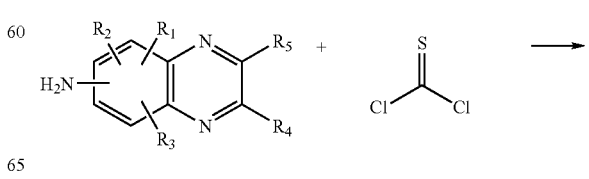

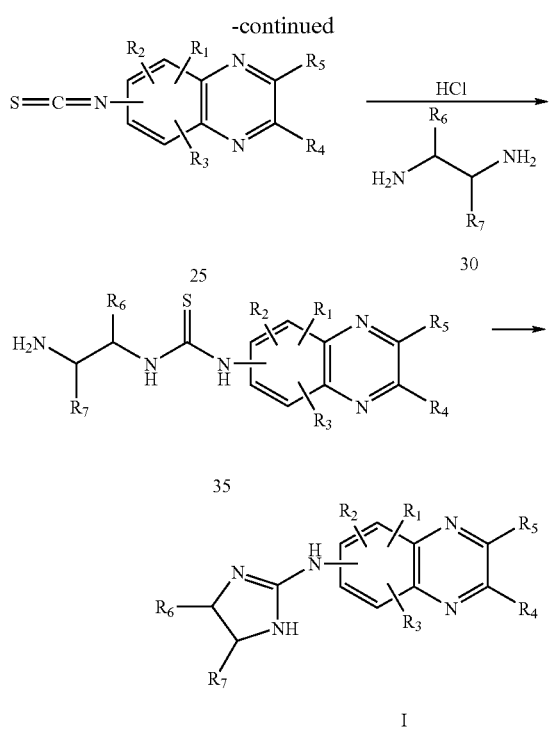

Compounds of the invention can be synthesized by reaction of the appropriate quinoxalines 15 with thiophosgene 20 to form corresponding isothiocyanates 25. The reaction with thiophosgene can be carried out in aqueous solution or in dilute aqueous hydrochloric acid at room temperature in a period of about 2 hours. Alternatively, the thiophosgene 20 dissolved in a water-immiscible solvent, such as chloroform, can be added to a basic aqueous solution (sodium carbonate) of quinoxalines 15 and stirred for about two hours. In the first alternative, isothiocyanates 25 precipitate from the reaction mixture. Precipitation can be completed by neutralization with excess aqueous base. Precipitated isothiocyanates 25 are recovered by filtration and dissolved in a suitable solvent, e.g., chloroform, to form a solution. The solution is dried (e.g., $MgSO_4$), filtered, and concentrated to yield the isothiocyanates 25.

Isothiocyanates 25 are treated with an excess of the appropriately substituted ethylene diamine to form the corresponding 3-quinoxalin-6-yl-thioureas 35. Isothiocyanates 25 are reacted with an excess (e.g., 5 moles to 1 mole) of ethylene diamine 30 in a suitable solvent, e.g., diethyl ether, benzene, chloroform or dioxane. The reaction is carried out at room temperature for about 2 hours. 3-Quinoxalin-6-yl-thioureas 35 precipitate and are recovered by filtration and washing the filter cake with solvent.

Cyclization of 3-quinoxalin-6-yl-thioureas 35 to afford compounds of the invention 10 is effected by heating a suspension of thioureas 35 with mercuric or cupric oxide in a suitable organic solvent, e.g., ethanol. The mercuric or cupric oxide can be replaced by an organic soluble mercuric or cupric salt, e.g., mercuric or cupric acetate. The reaction mixture is filtered, to remove the mercuric or cupric sulfide by-product, and the filtrate is concentrated to give compounds 10 in crude form. Compounds 10 are recrystallized as the free base or converted to an acid-addition salt by conventional reaction with a suitable acid. In certain cases, cyclization can be effected by simply refluxing the thioureas 35 in a suitable organic solvent, e.g., methanol, in the absence of mercuric or cupric oxide.

Quinoxalines 15 are synthesized by well-known synthetic procedures, for example, the procedures disclosed in J. A. JOULE ET AL., HETEROCYCLIC CHEMISTRY 189-224 (3rd ed. 1995), hereby incorporated herein by reference.

1.3 Topical Formulations of the Invention

In one embodiment, the compounds of the invention are delivered to the affected area of the skin in a pharmaceutically acceptable topical carrier. As used herein, a pharmaceutically acceptable topical carrier is any pharmaceutically acceptable formulation that can be applied to the skin surface for topical, dermal, intradermal, or transdermal delivery of a pharmaceutical or medicament. The combination of a pharmaceutically acceptable topical carrier and a compound of the invention is termed a topical formulation of the invention. Topical formulations of the invention are prepared by mixing a compound of the invention with a topical carrier according to well-known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

The topical carriers useful for topical delivery of compounds of the invention can be any carrier known in the art for topically administering pharmaceuticals, for example, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions, such as standard ophthalmic preparations.

1.3.1 Emulsions, Gels, and Ointments as Topical Carriers

In a preferred embodiment, the topical carrier used to deliver a compound of the invention is an emulsion, gel, or ointment. Emulsions, such as creams and lotions are suitable topical formulations for use in the invention. An emulsion is a dispersed system comprising at least two immiscible phases, one phase dispersed in the other as droplets ranging in diameter from 0.1 μm to 100 μm. An emulsifying agent is typically included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In another embodiment, the topical carrier used to deliver a compound of the invention is a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels for use with the invention are disclosed in U.S. Pat. Nos. 6,387,383 (issued May 14, 2002);

U.S. Pat. No. 6,517,847 (issued Feb. 11, 2003); and U.S. Pat. No. 6,468,989 (issued Oct. 22, 2002), each of which patents is hereby incorporated herein by reference.

Polymer thickeners (gelling agents) that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Preferably the gelling agent comprises between about 0.2% to about 4% by weight of the composition. More particularly, the preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STABILEZE®" is between 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

In another preferred embodiment, the topical carrier used to deliver a compound of the invention is an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

1.3.2 Aqueous Topical Formulations of the Invention

In another embodiment, the topical carrier used in the topical formulations of the invention is an aqueous solution or suspension, preferably, an aqueous solution. Well-known ophthalmic solutions and suspensions are suitable topical carriers for use in the invention. Suitable aqueous topical formulations for use in the invention are disclosed in REMINGTON: THE SCIENCE AND PRACTICE OF PHARMACY 1563-1576 (Alfonso R. Gennaro ed. 19th ed. 1995), hereby incorporated herein by reference. Other suitable aqueous topical carrier systems are disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002), all of which patents are hereby incorporated herein by reference.

The pH of the aqueous topical formulations of the invention are preferably within the range of from about 6 to about 8, more preferably, of from about 6.3 to about 6.5. To stabilize the pH, preferably, an effective amount of a buffer is included. In one embodiment, the buffering agent is present in the aqueous topical formulation in an amount of from about 0.05 to about 1 weight percent of the formulation. Acids or bases can be used to adjust the pH as needed. Suitable buffering agents are listed below in Section 1.3.3.

Tonicity-adjusting agents can be included in the aqueous topical formulations of the invention. Examples of suitable tonicity-adjusting agents include, but are not limited to, sodium chloride, potassium chloride, mannitol, dextrose, glycerin, and propylene glycol. The amount of the tonicity agent can vary widely depending on the formulation's desired properties. In one embodiment, the tonicity-adjusting agent is present in the aqueous topical formulation in an amount of from about 0.5 to about 0.9 weight percent of the formulation.

Preferably, the aqueous topical formulations of the invention have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In a preferred embodiment, the aqueous topical formulation of the invention is isotonic saline comprising a preservative, such as benzalkonium chloride or chlorine dioxide, a viscosity-adjusting agent, such as polyvinyl alcohol, and a buffer system such as sodium citrate and citric acid.

1.3.3 Excipients

The topical formulations of the invention can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin.

Chlorine dioxide ($ClO_2$), preferably, stabilized chlorine dioxide, is a preferred preservative for use with topical formulations of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995), hereby incorporated herein by reference, discloses a form of stabilized chlorine dioxide and a method for producing same, which can be used as a preservative for aqueous ophthalmic solutions and is useful in topical formulations of the invention. The manufacture or production of certain stabilized chlorine dioxide products is described in U.S. Pat. No. 3,278,447, hereby incorporated herein by reference. A commercially available stabilized chlorine dioxide which can be utilized in the practice of the present invention is the proprietary stabilized chlorine dioxide of BioCide International, Inc. of Norman, OK, sold under the trademark Purogene™ or Purite™. Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methyl pyrrolidone.

1.3.4 Pharmaceutical Additives

The topical formulations of the invention can include pharmaceuticals or their pharmaceutically acceptable salts, for example, but not limited to, topical corticosteroids and other anti-inflammatory agents, such as betamethasone, diflorasone, amcinonide, fluocinolone, mometasone, hydrocortisone, prednisone, and triamcinolone; local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

1.4 Dosage

Dosages and dosing frequency will be determined by a trained medical professional depending on the activity of the compound of the invention, the characteristics of the particular topical formulation, and the identity and severity of the dermatologic disorder treated or prevented.

In general, a compound of the invention is present in a formulation of the invention in an amount of from about 0.01 percent to about 5 percent of the total weight of the formulation, preferably, of from about 0.05 percent to about 1 percent, more preferably, of from about 0.1 percent to about 0.2 percent of the total weight of the formulation.

To treat or prevent rosacea, the topical formulations of the invention are topically applied directly to the affected area in any conventional manner well known in the art. For example, by dropper or applicator stick, as a mist via an aerosol applicator, via an intradermal or transdermal patch, or by simply spreading a formulation of the invention onto the affected area with fingers. Generally the amount of a topical formulation of the invention applied to the affected skin area ranges from about 0.1 g/cm$^2$ of skin surface area to about 5 g/cm$^2$, preferably, 0.2 g/cm$^2$ to about 0.5 g/cm$^2$ of skin surface area. Typically, one to four applications per day are recommended during the term of treatment.

1.5 Use of Topical Formulations of the Invention in Combination with Other Skin-Disorder Treatments The formulations of the invention can be used in combination with other treatments and medications to provide more effective treatment or prevention of rosacea and its symptoms. In a preferred embodiment, the topical formulations of the invention are used in combination with treatment regimens and medications well known for treatment of dermatologic disorders, such as those disclosed in THE MERCK MANUAL 811-830 (Keryn A. G. Lane et al. eds. 17th ed. 2001), hereby incorporated herein by reference.

Using a formulation or compound of the invention in combination with another medicament or treatment means administering a compound of the invention and the other medicament or treatment to a subject in a sequence and within a time interval such that they can act together to treat or prevent rosacea and its symptoms. For example, the compounds of the invention can be administered at the same time as the other medicament in the same or separate formulations or at different times.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation. Thus, the formulations of the invention can be administered together or at separate times with other medications or treatments.

In one embodiment, the topical formulations of the invention are used in combination with systemic administration of antibiotics or retinoids including, but not limited to, orally dosed antibiotics, such as tetracycline, minocin, minocycline, erythromycin, and doxycycline, and orally dosed retinoids such as isotretinoins (e.g., Accutane or Roaccutance).

In another embodiment, the topical formulations of the invention are used in combination with other topical treatments including, but not limited to, topical formulations consisting of metronidizole, hydrogen peroxide, benzoyl peroxide, lipoic acid, and azelaic acid, and sulfur preparations; topically dosed antibiotics, such as metronidazole, clindamycin, and erythromycin; topical retinoids such as tretinoin, adapalene, tazarotene; or topical steroids.

In another embodiment, the topical formulations of the invention are used in combination with mixed light pulse therapy (photoderm), pulsed dye laser treatment, or electrosurgery.

1.6 Article of Manufacture

Another aspect of the invention is an article of manufacture that comprises a topical formulation of the invention in a suitable container with labeling and instructions for use. The container can be a dropper or tube with a suitable small orifice size, such as an extended tip tube made of any pharmaceutically suitable material.

The topical formulations of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332.

Preferably, instructions are packaged with the formulations of the invention, for example, a pamphlet or package label. The labeling instructions explain how to administer topical formulations of the invention, in an amount and for a period of time sufficient to treat or prevent rosacea and its symptoms. The labeling instructions are an important aspect of the invention in that before a composition can be approved for any particular use, it must be approved for marketing by the United States Food and Drug Administration. Part of that process includes providing a label that will accompany the pharmaceutical composition that is ultimately sold. Preferably, the label includes the dosage and administration instructions, the topical formulation's composition, the clinical pharmacology, drug resistance, pharmacokinetics, absorption, bioavailability, and contraindications.

1.7 EXAMPLES

The following examples are provided for illustrative purposes only and are not to be construed as limiting the invention's scope in any manner.

1.7.1 Example 1

Synthesis of (5-Bromo-quinoxalin-6-yl)-(4,5-dihydro-1H-imidazol-2-yl)-amine

To a stirred solution of 6-amino-5-bromoquinoxaline hydrobromide (10 g) in distilled water (150 ml) is added thiophosgene (3 ml). The solution is stirred for two hours at room temperature and the resultant precipitate is collected by filtration, washed with water, and dried to afford 5-bromo-6-isothiocyanato-quinoxaline.

The 5-bromo-6-isothiocyanato-quinoxaline (3.5 g.) is directly dissolved in benzene (400 ml) and added dropwise to a well-stirred solution of ethylene diamine (15 g.) in benzene (50 ml). During a period of about two hours, an oil separates as a lower layer. The upper benzene layer is poured off and the oil is washed with diethyl ether and then dissolved in methanol (500 ml). The methanolic solution is refluxed until hydrogen sulfide evolution ceases. The methanolic solution is concentrated in vacuo to a volume of approximately 100 ml upon which a yellow solid precipitates. The precipitate is collected by filtration and recrystallized from methanol to afford of (5-Bromo-quinoxalin-6-yl)-(4,5-dihydro-1H-imidazol-2-yl)-amine: m.p. 250-251 C.

1.7.2 Example 2

An aqueous solution topical formulation of the invention comprises (5-Bromo-quinoxalin-6-yl)-(4,5-dihydro-1H-imidazol-2-yl)-amine-L-tartrate (brimonidine tartrate) (0.15 wt. %); Purite® (0.005%) (stabilized chlorine dioxide) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

1.7.3 Example 3

A aqueous solution topical formulation of the invention comprises (5-Bromo-quinoxalin-6-yl)-(4,5-dihydro-1H-imidazol-2-yl)-amine-L-tartrate, (brimonidine tartrate) (0.15 wt. %); benzalkonium chloride (0.005 wt. %) as a preservative; and the inactive ingredients: boric acid; calcium chloride; magnesium chloride; potassium chloride; purified water; sodium borate; sodium carboxymethylcellulose; sodium chloride; with hydrochloric acid and/or sodium hydroxide to adjust the pH to 5.6 to 6.6. The osmolality is in the range of 250-350 mOsmol/kg.

1.7.4 Example 4

A possible cream topical formulation of the invention is described in the Table below.

| Possible Cream Formulation Of The Invention (Hydrophilic Ointment USP) | |
|---|---|
| Ingredient | Weight Percent |
| Brimonidine tartrate | 0.15% |
| Stearic acid | 7% |
| Stearyl alcohol | 5% |
| Cetyl alcohol | 2% |
| Glycerin | 10% |
| Sodium lauryl sulfate | 1% |
| Propylparaben | 0.05% |
| Methylparaben | 0.25% |
| Disodium edetate | 0.055 |
| Distilled water | QS |

Melt the stearyl alcohol and the white petrolatum on a steam bath, and warm to about 75 degrees C. Add the other ingredients, previously dissolved in the water and warmed to 75 degrees C., and stir the mixture until it congeals. With stirring, allow the mixture to cool and add brimonidine tartrate as a concentrated solution.

1.7.5 Example 5

A possible ointment topical formulation of the invention is described in the Table below.

| Possible Ointment Formulation of the Invention (Hydrophilic Ointment USP) | |
|---|---|
| Ingredients | Weight |
| Brimonidine tartrate | 10 g |
| Cholesterol | 30 g |
| Stearyl Alcohol | 30 g |
| White Wax | 80 g |
| White Petrolatum | 850 g |

Mix the stearyl alcohol and white wax together on a steam bath, then add the cholesterol and stir until it completely dissolves. Add the white petrolatum and mix. Remove from the bath, and stir until the mixture congeals. Continue stirring and add brimonidine tartrate as a concentrated slurry.

1.7.6 Example 6

A possible gel formulation of the invention is described in the table below.

Possible Gel Formulation of the Invention

| Ingredients | Weight % |
|---|---|
| Brimonidine tartrate | 1.0% |
| Methylparaben NF | 0.15% |
| Propylparaben NF | 0.03% |
| Hydroxyethylcellulose NF | 1.25% |
| Disodium Edetate USP | 0.05% |
| Purified Water, USP | QS 100% |

1.7.7 Example 7

A possible gel formulation of the invention is described in the Table below.

Possible Gel Formulation of the Invention

| Ingredients | Weight % |
|---|---|
| Brimonidine tartrate | 1.0% |
| Methylparaben | 0.20% |
| Propylparaben | 0.05% |
| Carbomer 934P NF | 1.0% |
| Sodium Hydroxide | QS pH 7 |
| Purified Water USP | QS 100% |

The ingredients are mixed together and aqueous sodium hydroxide is slowly added to the mixture until a pH of about 7 is reached and the gel is formed.

1.7.8 Example 8

A possible gel formulation of the invention is described in the Table below.

Possible Gel Formulation of the invention

| Ingredients | Weight % |
|---|---|
| Brimonidine tartrate | 1.0% |
| Methylparaben | 0.2% |
| Propylparaben | 0.05% |
| "CARBOPOL ®" | 1.0% |
| Triethanolamine | QS pH 7 |
| Water | QS 100% |

The ingredients are mixed together and stirred. Triethanolamine is added until a pH of about 7 is attained.

1.7.9 Example 9

Alphagan P (0.15% brimonidine tartrate in isotonic saline and citrate buffer having a pH of 6.3 to 6.5) was supplied by Allergan, Inc. having the composition disclosed in Example 2 above. A study was conducted with four otherwise healthy persons who were independently diagnosed with phase II rosacea (characterized by transitory erythema of the mid-facial areas and early telangiectasis). All subjects followed a morning protocol of cleansing their face with soap and water. After a gentle towel drying and air drying, Alphagan-P was administered by gently rubbing onto areas of facial redness. The application area was again allowed to air dry without any dressing.

Subject 1 is a 59 year old woman with a ten year history of rosacea displaying symptoms of periodic redness flare-ups across her cheeks that usually runs a course of three to four weeks before subsiding under customary dermatological treatment. The subject showed an immediate improvement after the first morning application of Alphagan-P. All redness disappeared within 10 minutes and her face remained symptom free for the entire first day. Daily observation showed only mild return of redness after 24 hours. Continued daily use resulted in completely eliminating the redness due to rosacea in three days.

Subject 2 is a 54 year-old woman with an eight year history of rosacea who suffers from everyday facial redness across her cheeks with occasional severe flare-ups. The subject halted her customary daily dermatological treatment to try the protocol described above. The result was the same immediate removal of all redness within ten minutes. The dramatic improvement lasted most of the day with some mild redness re-occurring in the evening. For this subject, redness returned the next day. Continued daily use provided daily relief from redness.

Subject 3 is a 57 year-old man with a greater than ten-year history of rosacea displaying symptoms of redness of the cheeks and the nose. Although this subject's redness due to rosacea is always present, his general ruddy complexion and lack of concern allows him to forgo the daily use of customary dermatological treatment in favor of occasional, ad hoc treatments. A single morning trial of the Alphagan-P protocol described above resulted in dramatic daylong relief of redness.

Subject 4 is a woman in her early forties with a diagnosis of rosacea on her lower face and chin. Her condition includes some thickening of skin. Upon trying the protocol, redness was greatly reduced but not completely eliminated. Qualitatively the reduction was described as 80% less red. An additional observation of reduced skin thickening was reported.

These trials demonstrate that 0.15% brimonidine tartrate, when used in a daily morning protocol, dramatically eliminates or reduces redness due to rosacea. It is shown to be an effective treatment to greatly accelerate the arrest of a rosacea flare-up. It is further shown to be an effective daily treatment for chronic rosacea redness.

1.7.10 Example 10

Use of Oxymetazoline

An oxymetazoline solution (Afrin®, 0.05% solution. Schering-Plough HealthCare Products) The solution was placed onto a cotton tipped swab and applied to approximately 4 cm$^2$ of naso-facial skin displaying rosacea induced erythema. Twenty two minutes after application a lessening of erythema was observed.

1.7.11 Example 11

Use of Epinephrine

An epinephrine solution (Epipen®, trademark of Dey®, L.P.) containing approximately 0.3 mg of epinephrine was placed in a glass container. The solution was placed onto a cotton tipped swab and then applied to approximately 4 cm$^2$ of naso-facial skin displaying rosacea induced erythema. Within 5 minutes of application a mottled whitening of the skin was observed. No whitening was observed in skin outside of the application area. The whitening effect began to fade after approximately 30 minutes.

1.7.12 Example 12

A tetrahydrozoline solution (Visine®, 0.05% solution, Pfizer) The solution was placed onto a cotton-tipped swab and applied to approximately 4 cm² of naso-facial skin displaying rosacea induced erythema. Visual observation indicated no erythema reduction using this concentration of tetrahydrozoline.

1.7.13 Example 13

Testing Procedure for Prevention of Redness by α-Adrenergic Agonists:

A number of α-adrenergic agonists were evaluated for their ability to topically suppress erythema in human skin induced by methyl nicotinate. The erythema produced in the skin results from the vasodilatory effect on the dermal vasculature by methyl nicotinate. In this model, the minimum erythemal dose (MED) produced on the forearm by methyl nicotinate is determined for each test subject. The MED is defined as the minimal dose that results in a defined circle of erythema. The MED was determined by saturating five 19 mm Hill Top Chambers with 220 µl of 1, 2, 3, 4, and 5 mm methyl nicotinate. The Hill Top Chambers were applied to the volar forearm of each test subject, removed after 30 seconds and excess liquid lightly blotted from the skin. The MED of methyl nicotinate was selected 10 minutes after application, by determining the minimal dose that resulted in a defined circle of erythema. The α-adrenergic agonists were dissolved in alcohol and topically applied (2 µl/cm²) to selected sites on the contralateral volar forearm for 30 minutes prior to challenge with methyl nicotinate. Hill Top Chambers (19 mm) were saturated with 220 µl of the dose of methyl nicotinate determined to produce a MED for each test subject. The chambers were applied to the volar forearm treated with vehicle or test compounds, removed after 30 seconds and excess liquid was lightly blotted from the skin. Ten minutes after application of methyl nicotinate the test sites were evaluated for erythema. A numerical grading scale of 0 to 3 was used: 0=none, 0.5=barely perceptible, 1.0=mild, 1.5=mild+(mild to moderate), 2.0=moderate, 2.5=moderate+(moderate to severe), 3.0=severe.

The test results are shown in the table below and indicate that each of the tested compounds reduced the formation of the Methyl Nicotinate induced redness (erythema) in the test subjects. With both Oxymetazoline HCl and Naphazoline HCl the redness was fully blocked for two of the three subjects pursuant to the test conditions as described above.

The Effect of α-Adrenergic Agonists on Methyl Nicotinate-Induced Erythema

| Pre-Treatment + Methyl Nicotinate | N | Mean Erythema Grade |
|---|---|---|
| Alcohol Vehicle Control | 3 | 3.0 |
| 0.2% Naphazoline HCl | 3 | 0.33 |
| 0.2% Oxymetazoline HCl | 3 | 1.0 |
| 0.2% Brimonidine | 3 | 0.83 |

1.8 Definitions

The phrase "pharmaceutically acceptable salt(s)", as used herein, means those salts of compounds of the invention that are safe and effective for topical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

The term "pharmaceutically acceptable topical formulation" as used herein means any formulation which is pharmaceutically acceptable for topical delivery of the compounds of the invention. According to the invention, a "topical formulation" will comprise at least a compound of the invention. The choice of topical formulation will depend on several factors, including the nature of the symptoms to be treated or prevented, the physiochemical characteristics of the particular compound of the invention and of other excipients present, their stability in the formulation, available manufacturing equipment, and cost constraints.

As used herein, a "therapeutically effective amount of a compound of the invention" means the minimum amount of the compound that is effective to treat or prevent rosacea or its symptoms.

As used herein, the term "subject" means any animal, preferably a mammal, to which will be or has been administered compounds or topical formulations of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of treatment or prevention of rosacea or its symptoms.

The term "analog" refers to a chemical compound that is structurally similar to a parent compound and has chemical properties or pharmaceutical activity in common with the parent compound. Analogs include, but are not limited to, homologs, i.e., where the analog differs from the parent compound by one or more carbon atoms in series; positional isomers; compounds that differ by interchange of one or more atoms by a different atom, for example, replacement of a carbon atom with an oxygen, sulfur, or nitrogen atom; and compounds that differ in the identity of one or more functional groups, for example, the parent compound differs from its analog by the presence or absence of one or more suitable substituents. Suitable substituents include, but are not limited to, $(C_1-C_8)$alkyl; $(C_1-C_8)$alkenyl; $(C_1-C_8)$alkynyl: aryl; $(C_2-C_5)$heteroaryl; $(C_1-C_6)$heterocycloalkyl; $(C_3-C_7)$cycloalkyl; O—$(C_1-C_8)$alkyl; O—$(C_1-C_8)$alkenyl; O—$(C_1-C_8)$alkynyl; O-aryl; CN; OH; oxo; halo, C(O)OH; COhalo; O(CO)halo; $CF_3$, $N_3$; $NO_2$, $NH_2$; NH($(C_1-C_8)$alkyl); N($(C_1-C_8)$alkyl)$_2$; NH(aryl); N(aryl)$_2$ N($(C_1-C_8)$alkyl)(aryl); (CO)$NH_2$; (CO)NH($(C_1-C_8)$alkyl); (CO)N($(C_1-C_8)$alkyl)$_2$; (CO)NH(aryl); (CO)N(aryl)$_2$; O(CO)$NH_2$; NHOH; NOH($(C_1-C_8)$alkyl); NOH(aryl); O(CO)NH($(C_1-C_8)$alkyl); O(CO)N($(C_1-C_8)$alkyl)$_2$; O(CO)NH(aryl); O(CO)N(aryl)$_2$; CHO; CO($(C_1-C_8)$alkyl); CO(aryl); C(O)O($(C_1-C_8)$alkyl); C(O)O(aryl); O(CO)

$((C_1-C_8)$alkyl); $O(CO)$(aryl); $O(CO)O((C_1-C_8)$alkyl); $O(CO)O$(aryl); $S-(C_1-C_8)$alkyl; $S-(C_1-C_8)$alkenyl; $S-(C_1-C_8)$alkynyl; S-aryl; $S(O)C_1-C_8)$alkyl; $S(O)-(C_1-C_8)$alkenyl; $S(O)-(C_1-C_8)$alkynyl; and S(O)-aryl; $S(O)_2-(C_1-C_8)$alkyl; $S(O)_2-(C_1-C_8)$alkenyl; $S(O)_2-(C_1-C_8)$alkynyl; and $S(O)_2$-aryl. One of skill in the art can readily choose a suitable substituent based upon the stability and pharmacological activity of the compound of the invention.

The term "alkyl" means a saturated, monovalent, unbranched or branched hydrocarbon chain. Examples of alkyl groups include, but are not limited to, $(C_1-C_3)$alkyl groups, such as methyl, ethyl, propyl, isopropyl and $(C_4-C_8)$ alkyl groups, such as 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, heptyl, and octyl. An alkyl group can be unsubstituted or substituted with one or two suitable attachments.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl,2-propyl-2-butenyl,4-(2-methyl-3-butene)-pentenyl. An alkenyl group can be unsubstituted or substituted with one or two suitable substituents.

The term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl,4-propyl-2-pentynyl, and 4-butyl-2-hexynyl. An alkynyl group can be unsubstituted or substituted with one or two suitable substituents.

The term "aryl" means a monocyclic or polycyclic-aromatic group comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

The term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

The term "heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as $(C_1-C_6)$heterocycloalkyl.

The term "halogen" means fluorine, chlorine, bromine, or iodine. Correspondingly, the term "halo" means fluoro, chloro, bromo, and iodo.

The term "derivative" refers to an analog, as defined above, that is synthesized in one or more chemical reactions from its parent compound.

As used herein, the term "hydrate" means a compound of the invention, or a pharmaceutically acceptable salt thereof that further includes a stoichiometric or non-stoichiometric amount of water bound to it by non-covalent intermolecular forces.

In one embodiment, "treatment" or "treating" refers to an amelioration, prophylaxis, or reversal of a disease or disorder, or at least one discernible symptom thereof. For example, treating rosacea or its symptoms by lessening the redness of the skin. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compounds of the invention are administered as a preventative measure. As used herein, "prevention" or "preventing" refers to a reduction of the risk of acquiring a given disease or disorder. In a preferred mode of the embodiment, the compounds of the invention are administered as a preventative measure to a subject having a predisposition to rosacea even though symptoms of the disorder are absent or minimal.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342.

In view of the above Background, Summary, Figures, and Detailed Description, it is clear that in certain embodiments, the invention comprises a method of treating or preventing rosacea and its symptoms, comprising topically administering to the skin of a subject in need of such treatment or prevention a compound of a formula:

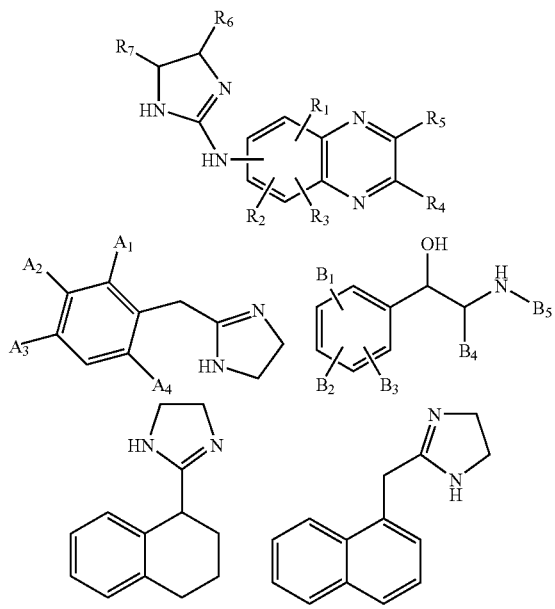

wherein each of $R_1$, $R_2$, and $R_3$ is independently hydrogen, halogen, alkyl, or alkoxy; each of $R_4$ and $R_5$ is independently hydrogen, alkyl, or alkoxy; and each of $R_6$ and $R_7$ is independently hydrogen, nitro, alkyl, or alkoxy;

wherein each of $A_1$, $A_3$, and $A_4$ is independently hydrogen or alkyl; and $A_2$ is independently hydrogen or hydroxy; and wherein each of $B_1$, $B_2$, and $B_3$ is independently hydrogen, hydroxy, or alkoxy; and each of $B_4$ and $B_5$ is independently hydrogen or alkyl.

All citations (e.g., scientific journal publications, patents, and other reference material) mentioned herein are hereby incorporated herein by reference to the same extent as if each individual citation was specifically and individually indicated to be incorporated by reference. One of ordinary skill in the art can make many variations and modifications to the above-described embodiments of the invention without departing from the spirit or scope of the appended claims. Accordingly, all such variations and modifications are within the scope of the appended claims.

What is claimed is:

1. A method of reducing redness associated with rosacea comprising topically administering a pharmaceutical composition comprising an effective amount of brimonidine or a pharmaceutically acceptable salt thereof to the site of the redness on the skin of a patient.

* * * * *